United States Patent
Capuano

(10) Patent No.: US 12,317,933 B2
(45) Date of Patent: *Jun. 3, 2025

(54) VARIABLE POWER CONTROL ELECTRONIC VAPING DEVICE

(71) Applicant: Altria Client Services LLC, Richmond, VA (US)

(72) Inventor: Sammy Capuano, Ramat Bet Shemesh (IL)

(73) Assignee: ALTRIA CLIENT SERVICES LLC, Richmond, VA (US)

( * ) Notice: Subject to any disclaimer, the term of this patent is extended or adjusted under 35 U.S.C. 154(b) by 419 days.

This patent is subject to a terminal disclaimer.

(21) Appl. No.: 17/857,462

(22) Filed: Jul. 5, 2022

(65) Prior Publication Data

US 2022/0400765 A1    Dec. 22, 2022

Related U.S. Application Data

(63) Continuation of application No. 16/361,743, filed on Mar. 22, 2019, now Pat. No. 11,399,569, which is a
(Continued)

(51) Int. Cl.
*A24F 40/50* (2020.01)
*A24F 40/57* (2020.01)
(Continued)

(52) U.S. Cl.
CPC .............. *A24F 40/50* (2020.01); *A24F 40/57* (2020.01); *A61M 15/06* (2013.01); *A24F 40/10* (2020.01)

(58) Field of Classification Search
None
See application file for complete search history.

(56) References Cited

U.S. PATENT DOCUMENTS

| 4,947,874 A | 8/1990 | Brooks et al. |
| 4,947,875 A | 8/1990 | Brooks et al. |

(Continued)

FOREIGN PATENT DOCUMENTS

| CN | 101366554 A | 2/2009 |
| CN | 101518361 A | 9/2009 |

(Continued)

OTHER PUBLICATIONS

International Preliminary Report on Patentability and Written Opinion of the International Searching Authority issued Aug. 13, 2013 for PCT Application No. PCT/US2012/024353 (4 pp).

(Continued)

*Primary Examiner* — Michael H. Wilson
*Assistant Examiner* — Daniel Edward Vakili
(74) *Attorney, Agent, or Firm* — Harness, Dickey & Pierce, P.L.C.

(57) ABSTRACT

Disclosed are an electronic cigarette and methods for controlling the power to the electronic cigarette which provides various modes of operation, including both regulated and no-regulated mode. The method is implemented m the form of an electronic power control program that controls the constituent parts of the electronic cigarette, including the battery, atomizer, heating element, smoke liquid or juice, and related circuitry.

13 Claims, 7 Drawing Sheets

Related U.S. Application Data continuation of application No. 13/962,584, filed on Aug. 8, 2013, now Pat. No. 10,238,143, which is a continuation of application No. PCT/US2012/024353, filed on Feb. 8, 2012.

(60) Provisional application No. 61/441,133, filed on Feb. 9, 2011.

(51) Int. Cl.
*A61M 15/06* (2006.01)
*A24F 40/10* (2020.01)

(56) References Cited

U.S. PATENT DOCUMENTS

| | | | |
|---|---|---|---|
| 5,372,148 | A | 12/1994 | McCafferty et al. |
| 5,881,714 | A | 3/1999 | Yokoi et al. |
| 6,040,560 | A | 3/2000 | Fleischhauer et al. |
| 2004/0187869 | A1 | 9/2004 | Bjorndal et al. |
| 2008/0092912 | A1 | 4/2008 | Robinson et al. |
| 2008/0190422 | A1 | 8/2008 | Nobutani et al. |
| 2009/0025718 | A1 | 1/2009 | Denyer et al. |
| 2010/0024974 | A1 | 2/2010 | Narita |
| 2010/0242974 | A1 | 9/2010 | Pan |
| 2010/0313901 | A1 | 12/2010 | Fernando et al. |
| 2011/0036346 | A1 | 2/2011 | Cohen et al. |
| 2011/0265806 | A1 | 11/2011 | Alarcon et al. |

FOREIGN PATENT DOCUMENTS

| | | | |
|---|---|---|---|
| DE | 102009029768 A1 | 1/2011 | |
| EP | 0358002 A2 | 3/1990 | |
| EP | 0358114 A2 * | 3/1990 | ............ A61M 15/00 |
| EP | 0430566 A2 | 6/1991 | |
| EP | 2 047 880 | 4/2009 | |
| EP | 2110033 A1 | 10/2009 | |
| EP | 2253233 A1 | 11/2010 | |
| EP | 2460423 A1 | 6/2012 | |
| JP | 2001-502542 A | 2/2001 | |
| WO | WO-98/17131 A1 | 4/1998 | |
| WO | WO-2008/015918 A1 | 2/2008 | |
| WO | WO-2009/118085 A1 | 10/2009 | |

OTHER PUBLICATIONS

International Search Report mailed Sep. 7, 2012 for PCT Application No. PCT/US2012/024353 (3 pp).
Office Action for corresponding Chinese Application No. 2012-80012152.2 dated Sep. 14, 2015, and English translation thereof.
Office Action for corresponding Japanese Application No. 2013-553526 dated Dec. 3, 2015, and English translation thereof.
Third Party Observation Notice dated Aug. 3, 2016 issued in corresponding European Application No. 12744237.4.
Communication from the European Patent Office corresponding to Application No. 12 744 237.4-1808 dated Aug. 3, 2017.
Office Action for corresponding European Application No. 12744237.4 dated Nov. 6, 2017.
Korean Office Action for corresponding Korean Application No. 10-2013-7023466 dated Apr. 11, 2018.

* cited by examiner

| Mode Name | Pre-Set "Pause" Duration Range for Mode | Output Voltage during Mode | Minimum Energizing Duration of Mode |
|---|---|---|---|
| Self-Priming Mode | 30+ seconds | A value up to the battery's maximum Unregulated voltage potential | 5 seconds |
| Regulated Mode | 4 - 29 seconds | Regulated at 3.0 volts | no min. set |
| Safety Mode | 0 - 3 seconds | Regulated at 2.8 volts | no min. set |

Figure 2

| Mode Name | Pre-Set "Pause" Duration Range for Mode | Output Voltage during Mode | Minimum Energizing Duration of Mode |
|---|---|---|---|
| Self-Priming Mode 1 | 40+ seconds | A value up to the battery's maximum unregulated voltage potential | 6 seconds |
| Self-Priming Mode 2 | 30 - 40 seconds | Regulated at 3.5 volts | 5 seconds |
| Regulated Mode | 4 - 29 seconds | Regulated at 3.0 volts | no min. set |
| Safety Mode 1 | 3 seconds | Regulated at 2.9 volts | no min. set |
| Safety Mode 2 | 2 seconds | Regulated at 2.8 volts | no min. set |
| Safety Mode 3 | 0, 1 second | Regulated at 2.6 volts | no min. set |

Figure 3

| Mode Name | Pre-Set Temp. Range for Mode | Output Voltage during Mode | Minimum Energizing Duration of Mode |
|---|---|---|---|
| Self-Priming Mode 1 | 0° - 15° C | A value up to the battery's maximum Unregulated voltage potential | 7 seconds |
| Self-Priming Mode 2 | 16° - 25° C | Regulated at 3.5 volts | 5 seconds |
| Regulated Mode | 26° - 50° C | Regulated at 3.0 volts | no min. set |
| Safety Mode 1 | 51° - 65° C | Regulated at 2.9 volts | no min. set |
| Safety Mode 2 | 66° - 80° C | Regulated at 2.8 volts | no min. set |
| Safety Mode 3 | 81°+ C | Regulated at 2.6 volts | no min. set |

Figure 4

VARIABLE POWER CONTROL ELECTRONIC VAPING DEVICE

PRIORITY CLAIM

This application is a Continuation of U.S. application Ser. No. 16/361,743, filed Mar. 22, 2019, which is a Continuation of U.S. application Ser. No. 13/962,584, filed Aug. 8, 2013, which is a Continuation of PCT Application No. PCT/US2012/024353, filed on Feb. 8, 2012, which claims priority to U.S. Provisional Patent Application No. 61/441,133, filed on Feb. 9, 2011, the entire contents of each of which are incorporated herein by reference.

TECHNICAL FIELD

This invention relates generally to electronic cigarettes and more specifically to a variable power control program for electronic cigarette systems.

BACKGROUND ART

Electronic cigarettes are becoming a popular alternative to tobacco smoking because of the many advantages that they offer. The advantages of electronic cigarettes may include the absence of tar, odor, ash, pollution, and combustion by-products as compared, to traditional tobacco smoking, However, there are still several factors holding users back from fully embracing this promising device. The addiction to smoking is not simply an addiction to nicotine; it is a habit that has many facets, including physiological, psychological, social, tactile, etc. Therefore, a large part of creating an ideal electronic cigarette is to provide a positive user experience which is increasingly similar to tobacco smoking. This means that the electronic cigarette has to require minimal priming, produce consistent "smoke" volume, and always be available with reliable and extended battery life.

An electronic cigarette typically comprises a battery, an atomizer, a container having smoke juice, and a power control circuit. The battery is used to power the circuit and the atomizer, where the atomizer heats the smoke juice to create smoke to vapor, which is inhaled by a user. "Smoke" volume is dependent on the power output of the device, which is a function of voltage squared, divided by the resistance. Accordingly, in the usual arrangement, battery output voltage is directly proportional to "smoke" volume.

Earlier versions of electronic cigarettes often failed to provide positive user experience, Most electronic cigarettes have unregulated lithium-polymer battery cells that start off with a high voltage of about 4.2 volts, and drops gradually to about 3.0 volts as the cell's charge is depleted. This arrangement relies on the battery's natural power degradation to regulate the production of smoke, Thus, as the battery cell is depleted, voltage in the battery naturally decreases and the "smoke" volume noticeably drops, making for an inconsistent smoking experience.

Another disadvantage with these unregulated electronic cigarettes is that the power supplied during power-up or priming" are very high, tending to produce excessive heat. After priming, the battery continues operating at its maximum output (minus any power loss due to the priming stage) and the excessive heat produced does not have enough time to dissipate, resulting in high internal and external temperatures on the housing of the cartridge. It often happens that after a dozen or so puffs, the smoke juice and materials surrounding the heating element start to overheat and acquire an unpleasant burning smell. More concerning, the atomizer housing becomes so hot that it can burn the fingers and/or lips of the user.

Newer versions of electronic cigarettes often incorporate a circuit to reduce output power at specific points during operation by regulating the output voltage of the battery at all times during operation. The purpose of regulation is to limit the output voltage of the battery throughout the smoking cycle to the same voltage level that the battery will have at its depleted state (i.e., at approximately 3 volts), thereby maintaining a uniform lower output voltage. This is supposed to ensure that the user has a uniform experience from the first puff to the last, with no degradation in "smoke" volume as the battery discharges, while conserving energy and extending battery life.

Unfortunately, there is a downside to this approach. In order for an atomizer to produce enough "smoke" volume, it needs to be sufficiently warmed up, which is hard to achieve in a short period of time when the battery output voltage is initially limited by the regulating circuit. A regulated voltage arrangement therefore requires more time during the priming stage in order to warm up the atomizer, and, if the user takes a puff before the atomizer is completely primed, it leads to less smoke/vapor production at the beginning, thereby impairing user experience because the initial puffs are not satisfying. Moreover, these initial user puffs essentially act as the "priming" for the device. For a first-time user of the electronic cigarette, the first few weak puffs—with little "smoke" volume—could be a disappointing experience, causing him to reject the product. It simply is not desirable for the user to be responsible for priming the device, as it can be a nuisance. Therefore, neither the unregulated system, nor the fully regulated system is a sufficient solution to ensure an optimal smoking experience and long battery life. Accordingly, there is a need in the art for a more dynamic or variable power control program that can provide a better smoking experience for the user.

SUMMARY OF THE INVENTION

The invention comprises an electronic cigarette and methods for controlling the power to the electronic cigarette which provides various modes of operation, including both regulated and un-regulated mode. The method is implemented in the form of an electronic power control program that controls the constituent parts of the electronic cigarette, including the battery, atomizer, heating element, smoke liquid or juice, and related circuitry.

BRIEF DESCRIPTION OF DRAWINGS

FIG. 2 is a table depicting the characteristics of the various modes of operation for one embodiment of the present invention.

FIG. 3 is a table depicting the characteristics of the various modes of operation for another embodiment of the present invention.

FIG. 4 is a table depicting the characteristics of the various modes of operation for another embodiment of the present invention, based on temperature feedback.

DETAILED DESCRIPTION OF THE EMBODIMENTS

The invention in embodiments thereof discloses an electronic cigarette and methods for controlling the power to an electronic cigarette which provides various modes of operation, including both regulated and unregulated mode. The method is implemented in the form of an electronic power control program that controls the constituent parts of the electronic cigarette, including the battery, atomizer, heating element smoke liquid or juice, and related circuitry.

When an electronic cigarette is first called into operation, it needs to be warmed up before the atomizer can produce smoke or vapor. Therefore, some embodiments of the power control program of the present invention have a first mode of operation, known as the "self-priming mode," which permits the heating element to be initially warmed up to the battery's maximum output voltage. This automatic "priming" mode reduces or completely eliminates the need for a user to manually prime the device. The "self-priming mode" is configured such that the heating element remains active for a pre-determined amount of time in order to assure proper priming. For example, as shown in FIG. 1, when the smoker initiates the first puff, the "self-priming mode" is initiated and the battery produces up to its maximum voltage (in this case, 4.2 V) for a predetermined amount of time (in this case, 5 seconds), even if the user activates the sensor for less than the predetermined amount of time.

Figure 1:
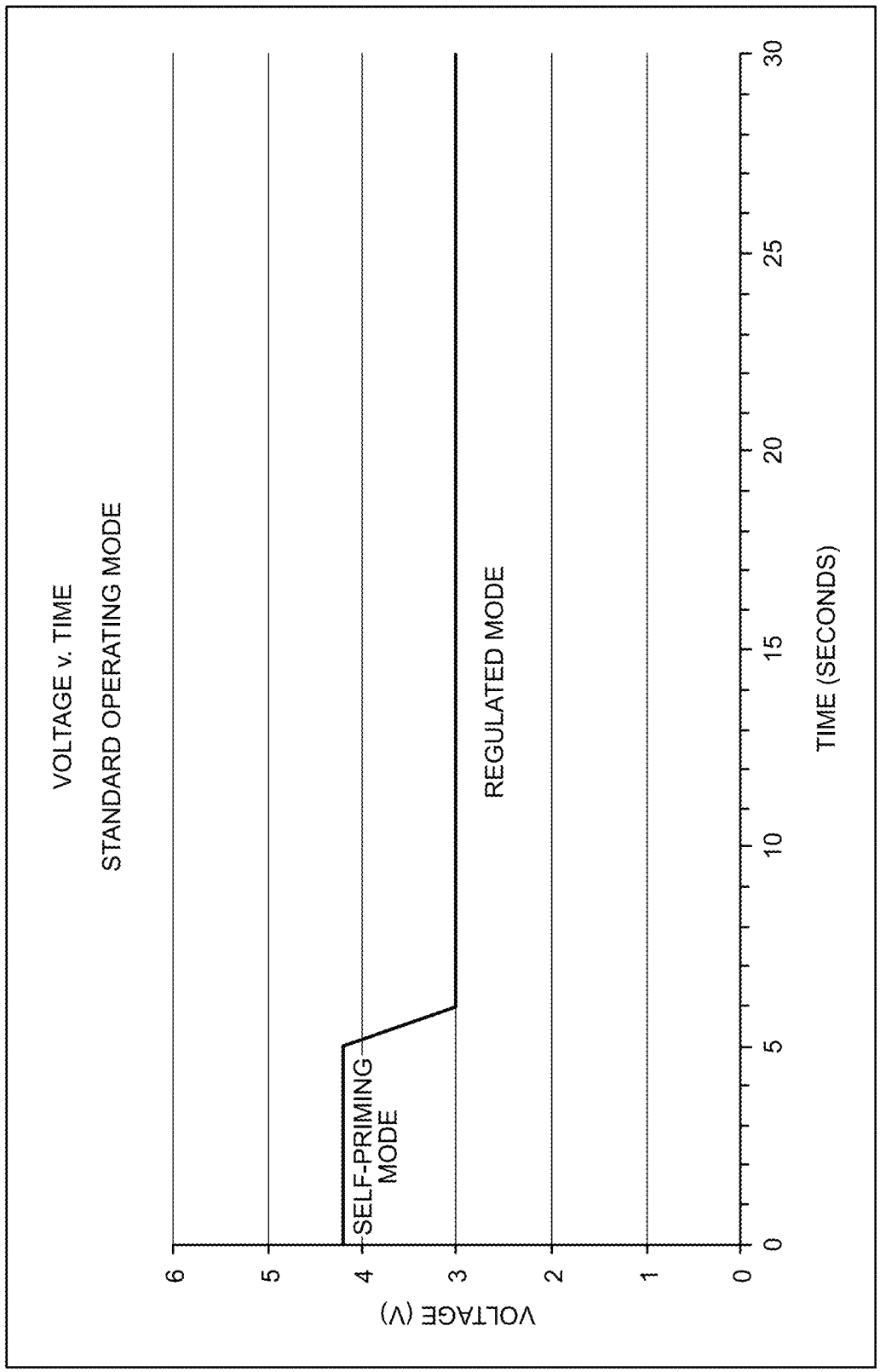
FIG. 1 is an exemplary voltage versus time plot, depicting the response of one embodiment of the present invention.

If a consecutive puff follows within a short time after the one before it, then there is no need to "prime" the heating element again, and the power control program can switch, to the "regulated mode." By example, FIG. 1 depicts activation of "regulated mode" after 5 seconds, at 3 V. This "regulated mode" conserves battery power while normalizing "smoke" volume to a constant level, providing a uniform smoking experience. However, it is understood that, in some embodiments, it is only desirable to stay in "regulated" mode if one is smoking at normal intervals. Thus, if a user takes a long pause between puffs, then it is preferable to switch back to "self-priming mode" because the heating element has cooled off to the point where the voltage supplied in the "regulated mode" is insufficient to produce the proper amount of smoke and/or vapor. Accordingly, in some embodiments, mode selection may be dictated by the length of time between puffs.

In some embodiments, a third mode, called "safety mode" may be activated in certain, circumstances. For example, if consecutive puffs are too close together in time, the atomizer might accumulate too much heat, causing it to overheat. Therefore, the power control program is adapted to trigger a "safety mode," where the voltage is dropped below the nominal voltage during "regulated mode." "Safety mode," therefore, will provide just enough power to evaporate additional smoke juice, but not enough power to cause excessive heat accumulation and/or an increase in temperature of the component parts of the electronic cigarette.

In accordance with the embodiments of the present invention that are time-based, the lapse between puffs or the "pause" determines which mode should be used to power the current puff. Each mode has "pause" value or a range of pause values associated with it, so that for each pause between puffs, the control program can identify which power mode should be triggered for that specific puff(s). FIG. 2 presents data from one such embodiment of the present invention, utilizing three modes of operation, "self-priming mode" "regulated mode," and "safety mode."

Another aspect of the present invention provides that the power control program receives feedback as to when a puff is initiated and when it ends. In some embodiments, this information is fed back to the control program from an air-flow sensor in the electronic circuit, which is activated based on user inhalation. Accordingly, a timing mechanism may be in communication with the air-flow sensor such that the timing mechanism is activated after the completion of every puff, and measures the time between puffs, i.e. "pause" (the timing mechanism is restarted after every puff). Accordingly, the power control program includes the ability to compare the measured pause against the pre-set pause range of each mode, to determine which mode should be triggered for the current puff. Also contemplated is a mechanism that can instantaneously adjust the output voltage according to the pre-assigned settings for a specific mode.

There are many common factors that determine the pause values of the modes and the output voltage level during each mode. Both the pause values and output voltage depend on thermal characteristics of the electronic cigarette including its construction, the configuration of its elements, material makeup of its components, its heat loss coefficient, as well as ambient temperature, pressure and other such factors. For example, frequent puffing does not allow enough time for the electronic cigarette to cool down, which affects the cumulative temperature of the unit. Electrical resistance of the heating element also greatly affects output voltage, because output voltage is inversely proportional to the electrical resistance. The construction of the electronic cigarette also affects how the passing air cools the heating element within the body of the cigarette. Further, the material makeup of the components affects the heat dissipation characteristics. All of these factors must he considered with determining the pause values of the particular modes for a given electronic cigarette configuration.

In one example, the pause value ranges and output voltage of the operation modes are pre-programmed into the microprocessor or microchip that comprise the power control program in the electronic cigarette. To determine those settings, actual tests are performed on the specific electronic cigarette by varying the pause between puffs and output voltage. Empirical data is gathered and optimal settings are selected based on the data. Presently available data shows that for most atomizers known in the art, where the internal resistance ranges from 2.2 ohms to 3.6 ohms, the "self-priming mode" is best set to run for 5 seconds (even if the user puffs less than that), and the output voltage should be non-regulated, i.e. the maximum output voltage of the battery. In some embodiments, the pause range for the "self-priming mode" should ideally be 30 seconds to infinity, meaning that the device remains in "self-priming mode" unless the next puff occurs within 30 seconds of the initial puff. Thus, it is not necessary to keep the timing mechanism measuring time beyond 30 seconds, because the pause value of 30 seconds already means that the atomizer is cooled off, and there is no need to waste battery power to run the timer. Instead, the power control program is adapted to stop the clock at 30 seconds. When a new puff is detected, the program checks either if the timer has stopped counting or if it is at 30 seconds, and if yes, it re-triggers the "self-priming mode."

Figure 6:
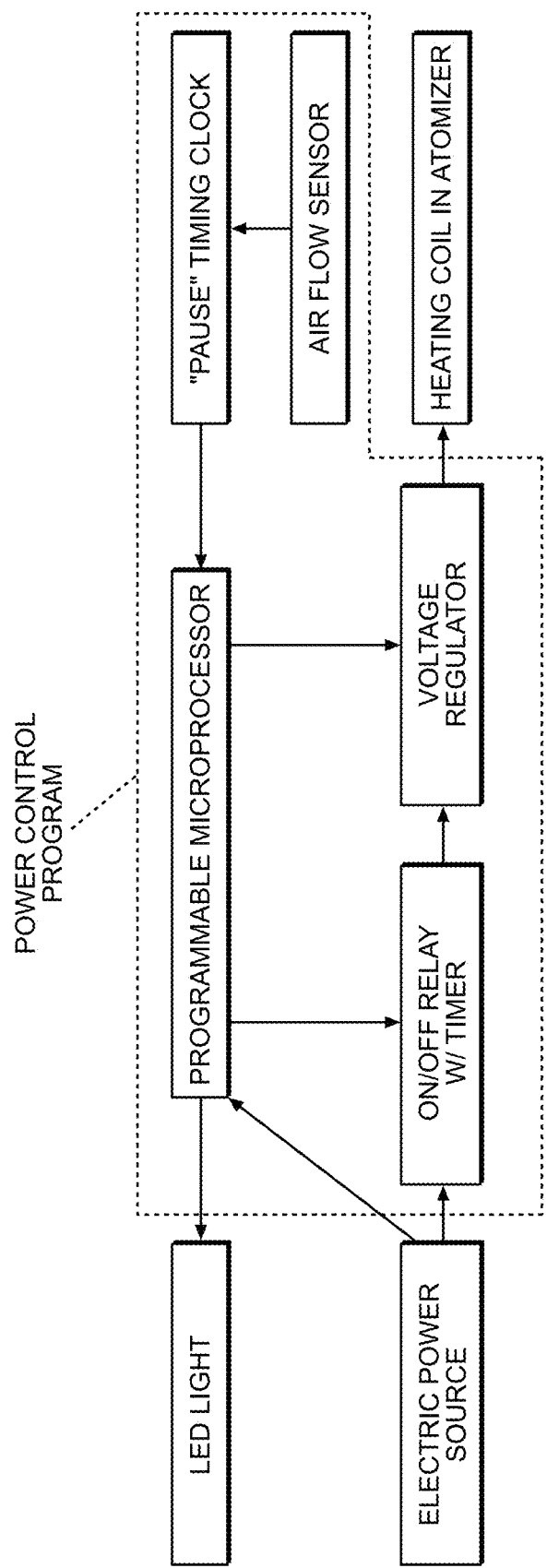
FIG. 6 is a schematic of the circuitry inside an electronic cigarette which contains an embodiment of Power Control Program in which the power mode are preset and determined by "Pause" duration.

If the new puff occurs less than 30 seconds from the initial puff, a different mode, i.e. "regulated mode" or "safety mode" of operation should be initiated. Accordingly, in some embodiments and for exemplary purposes, the ideal pause value range for "regulated mode" is 4 to 29 seconds, and the voltage should be regulated at 3.0 volts. In some embodiments, the ideal pause range value for "safety mode" is 0 to 3 seconds, and the voltage should be regulated at 2.8 volts. FIGS. 2 and 6 depict this configuration.

In further embodiments of the present invention, there are additional modes pre-programmed into the power control program. For example, the "safety" mode can be broken down further into several modes, each one having its own pause range and power output. Also, there could be several "self-priming" modes, depending on the pause duration and the cooling of the atomizer. FIGS. 3 and 6 depict this configuration. Accordingly, it is understood that the power control program of the present invention need not be limited to a certain number of power modes, rather any number of modes may be implemented as desired.

Figure 5:
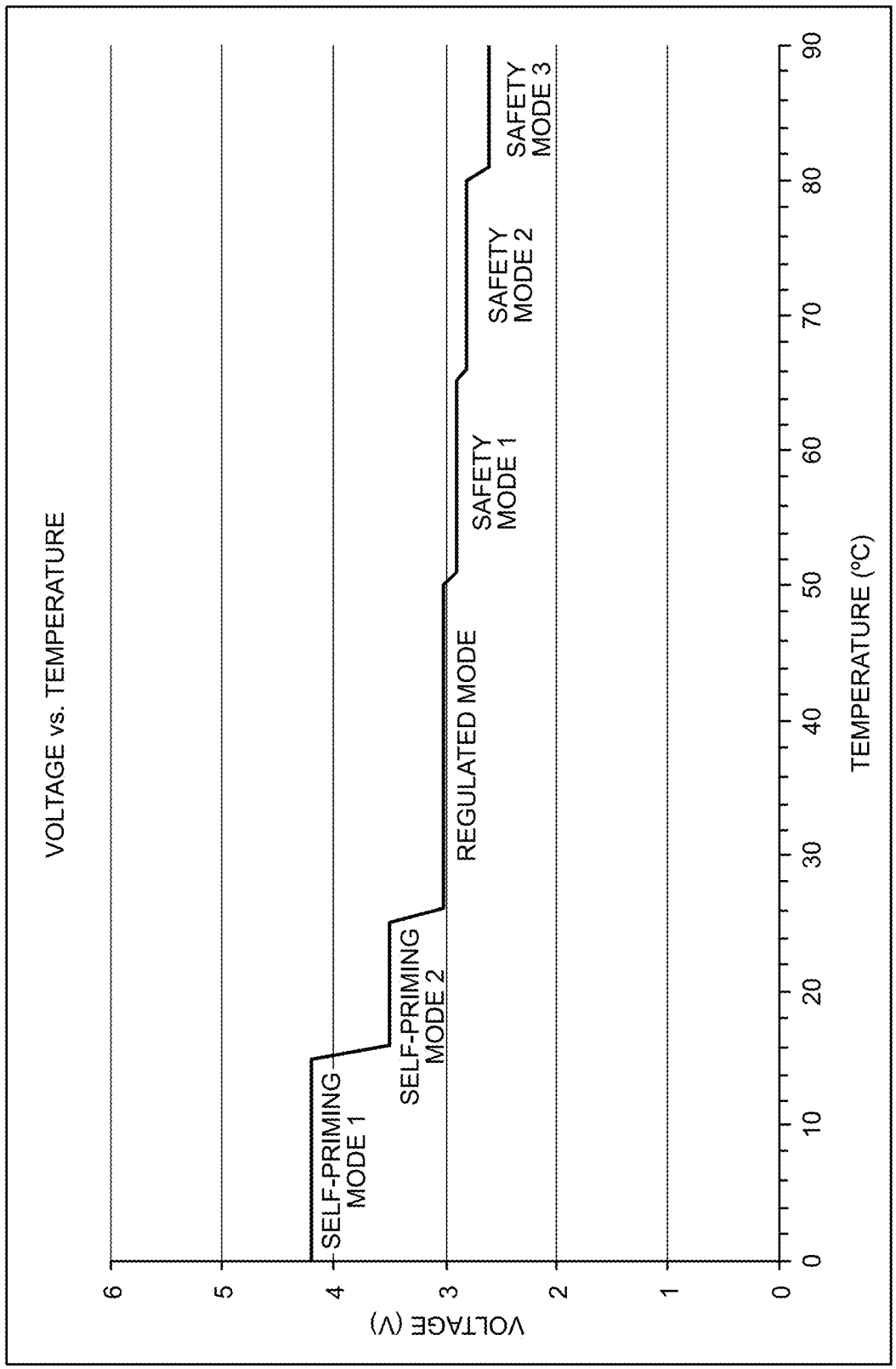
FIG. 5 is an exemplary voltage versus temperature plot, depicting the response of another embodiment of the present invention.
Figure 7:
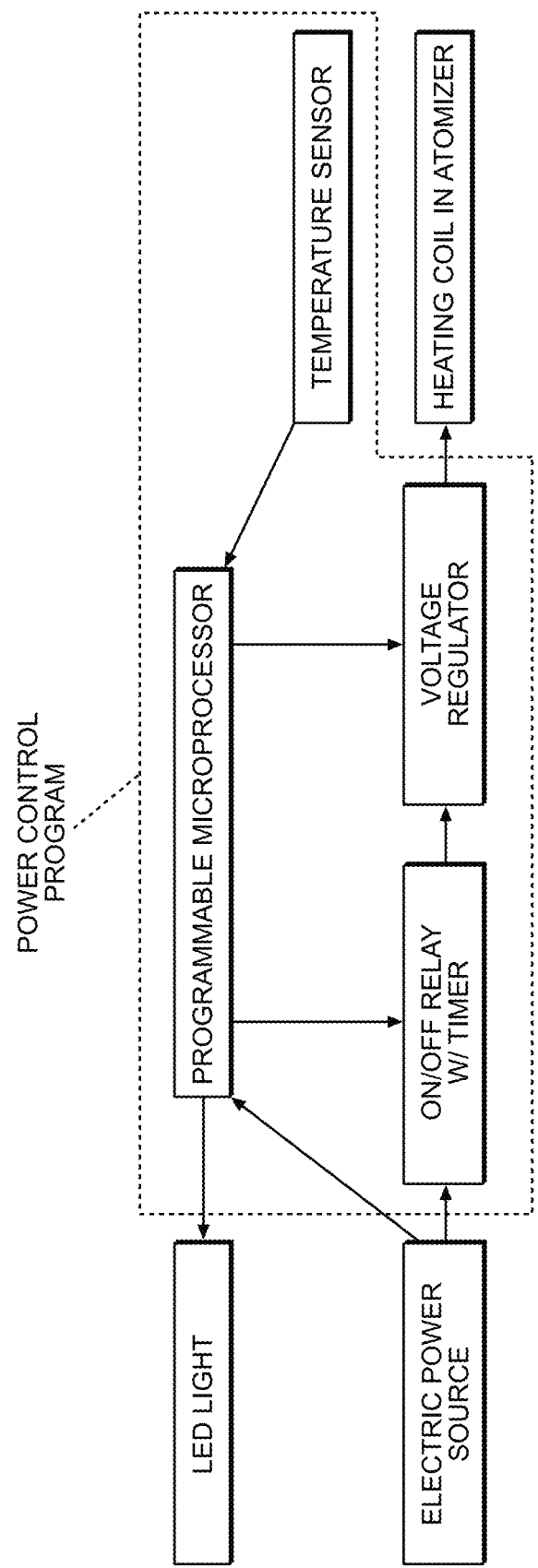
FIG. 7 is a schematic of the circuitry inside an electronic cigarette which contains an embodiment of Power Control Program, in which the power modes are preset and determined by a temperature feedback loop.

In further embodiments of the present invention, the modes of operation of the power control circuit are dynamic and/or reactive rather than pre-programmed. In these embodiments, the power output of the mode is pre-programmed, but the pause range values are replaced by a temperature feedback system. Instead of measuring time between puffs, the power control program receives temperature reading from temperature sensor/sensors inside the electronic cigarette, and it calculates which mode the current puff should trigger. In such an embodiment, the power control program has each temperature range assigned to a specific mode of operation. In some embodiments, the output voltage is adjusted at every puff, depending on the real-time temperature of the atomizer. FIGS. 4, 5, and 7 depict an example of this configuration.

It will be understood that the preferred embodiments of the present invention have been disclosed by way of example and that other modifications and alterations may occur to those skilled in the art without departing for the scope of the disclosure herein.

The invention claimed is:

1. An electronic vaping device comprising:
   a heating element;
   a power source configured to apply a voltage to the heating element;
   a sensor configured to sense airflow; and
   a processor configured to,
   control the power source to apply a first voltage to the heating element for at least a first time interval in response to the sensed airflow regardless of whether the sensed airflow stops before expiration of the first time interval,
   control the power source to apply a second voltage to the heating element based on the sensed airflow, and stop application of the second voltage to the heating element in response to cessation of the sensed airflow, the first voltage being greater than the second voltage, and
   control the power source to apply a third voltage to the heating element based on the sensed airflow, and stop application of the third voltage to the heating element in response to cessation of the sensed airflow, the second voltage being greater than the third voltage, and the third voltage being a non-zero voltage.

2. The electronic vaping device of claim 1, wherein the processor is configured to control the power source to apply the first voltage in response to initial sensing of the sensed airflow by the sensor.

3. The electronic vaping device of claim 1, wherein the processor is configured to control the power source to apply the second voltage in response to determining that a time between two puffs is greater than a first amount of time and less than a second amount of time.

4. The electronic vaping device of claim 3, wherein the processor is configured to control the power source to apply the third voltage in response to determining that the time between two puffs is in less than the first amount of time.

5. The electronic vaping device of claim 1, wherein the processor is further configured to switch between the first voltage, the second voltage, and the third voltage based on the sensed airflow and one of a time between puffs, a temperature of the electronic vaping device, or a combination of the time between puffs and the temperature of the electronic vaping device.

6. The electronic vaping device of claim 1, wherein the power source includes a battery.

7. An electronic vaping device comprising:
   a heating element;
   a power source configured to apply a voltage to the heating element;
   a sensor configured to sense airflow; and
   a processor configured to,
   control the power source to apply a first voltage based on the sensed airflow,
   control the power source to apply a second voltage after applying the first voltage, the first voltage being greater than the second voltage, and
   control the power source to apply a third voltage in a safety mode after applying the second voltage, the second voltage being greater than the third voltage, and the third voltage being a non-zero voltage, wherein,
   in the safety mode, the processor is further configured to control the heating element to heat a liquid enough to evaporate the liquid while also limiting accumulation of heat within the electronic vaping device.

8. The electronic vaping device of claim 7, wherein the processor is configured to control the power source to apply the first voltage in response to initial sensing of the sensed airflow by the sensor.

9. The electronic vaping device of claim 7, wherein the processor is configured to control the power source to apply the second voltage in response to determining that a time between two puffs is greater than a first amount of time and less than a second amount of time.

10. The electronic vaping device of claim 9, wherein the processor is configured to control the power source to apply the third voltage in the safety mode in response to determining the time between two puffs is less than the first amount of time.

11. The electronic vaping device of claim 7, wherein the processor is further configured to
   apply the first voltage in a first operating mode,
   apply the second voltage in a second operating mode, and
   switch between the first operating mode, the second operating mode and the safety mode based on the sensed airflow and one of a time between puffs, a temperature of the electronic vaping device, or a combination of the time between puffs and the temperature of the electronic vaping device.

12. The electronic vaping device of claim 7, wherein the power source includes a battery.

13. The electronic vaping device of claim 7, wherein the processor is configured to control the power source to apply the first voltage to the heating element for at least a first time interval in response to the sensed airflow regardless of whether the sensed airflow stops before expiration of the first time interval.

\* \* \* \* \*